United States Patent
Petersen et al.

(10) Patent No.: US 7,190,985 B2
(45) Date of Patent: Mar. 13, 2007

(54) OXIMETER AMBIENT LIGHT CANCELLATION

(75) Inventors: Ethan Petersen, Castro Valley, CA (US); William Shea, Livermore, CA (US); Bradford B. Chew, San Ramon, CA (US)

(73) Assignee: Nellcor Puritan Bennett Inc., Pleasanton, CA (US)

( * ) Notice: Subject to any disclaimer, the term of this patent is extended or adjusted under 35 U.S.C. 154(b) by 339 days.

(21) Appl. No.: 10/787,854

(22) Filed: Feb. 25, 2004

(65) Prior Publication Data

US 2005/0187448 A1  Aug. 25, 2005

(51) Int. Cl.
*A61B 5/00* (2006.01)

(52) U.S. Cl. .................. 600/336; 600/322; 600/323
(58) Field of Classification Search ........... 600/310, 600/322, 323, 336
See application file for complete search history.

(56) References Cited

U.S. PATENT DOCUMENTS

| | | | |
|---|---|---|---|
| 4,781,195 A | 11/1988 | Martin | |
| 4,802,486 A | 2/1989 | Goodman et al. | |
| 4,911,167 A | 3/1990 | Corenman et al. | |
| 4,928,692 A | 5/1990 | Goodman et al. | |
| 4,934,372 A | 6/1990 | Corenman et al. | |
| 5,351,685 A | 10/1994 | Potratz | |
| 5,368,026 A | 11/1994 | Swedlow et al. | |
| 5,368,224 A | 11/1994 | Richardson et al. | |
| 5,645,060 A | 7/1997 | Yorkey | |
| 5,662,106 A | 9/1997 | Swedlow et al. | |
| 5,713,355 A | 2/1998 | Richardson et al. | |
| 5,746,697 A | 5/1998 | Swedlow et al. | |
| 5,803,910 A | 9/1998 | Potratz | |
| 5,846,190 A | 12/1998 | Woehrle | |
| 5,885,213 A | 3/1999 | Richardson et al. | |
| 5,921,921 A | 7/1999 | Potratz et al. | |
| 5,924,979 A | 7/1999 | Swedlow et al. | |
| 5,954,644 A * | 9/1999 | Dettling et al. ............ | 600/322 |
| 6,226,539 B1 | 5/2001 | Potratz | |
| 6,385,471 B1 | 5/2002 | Mortz | |
| 6,449,501 B1 | 9/2002 | Reuss | |
| 2001/0002206 A1 | 5/2001 | Diab et al. | |
| 2002/0128544 A1* | 9/2002 | Diab et al. ................ | 600/323 |
| 2003/0028357 A1 | 2/2003 | Norris et al. | |

* cited by examiner

*Primary Examiner*—Eric Winakur
*Assistant Examiner*—Etsub Berhanu

(57) ABSTRACT

A pulse oximeter method and apparatus which provides (1) a notch filter at a distance between a modulation frequency and a common multiple of commonly used power line frequencies (50, 60, 100 and 120) and also (2) a demodulation frequency greater than a highest pulse rate of a person and lower than any harmonic of 50, 60, 100 or 120 Hz, to filter ambient light interference, while choosing an optimum demodulation frequency that avoids interference from the notch filter or from harmonics of the line interference. Also, ambient light for any low frequency interference, such as power line interference, is measured both before and after each of the light emitter wavelengths and the average of the ambient light is then subtracted from the detected signal.

25 Claims, 3 Drawing Sheets

$$Red = RedMod - \frac{Dark1 + Dark2}{2}$$

$$IR = IRMod - \frac{Dark2 + Dark3}{2}$$

OXIMETER AMBIENT LIGHT CANCELLATION

BACKGROUND OF THE INVENTION

The present invention relates to oximeters, and in particular to techniques for ambient light cancellation in pulse oximeters.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

One problem with oximeter measurements is that in addition to receiving the light that was directed at the tissue, ambient light is also detected by the photodetector. Attempts can be made to block out ambient light, but some amount of ambient light will typically be detected. One particular concern is the light at the power line frequency of fluorescent or other lights, which is 60 Hz in the United States and 50 Hz in Europe and other countries.

Since a single photodetector is typically used, the light of different wavelengths, such as red and infrared, is time multiplexed. The detected signal must be demultiplexed. The demultiplexing frequency must be high enough so that it is much larger than the pulse rate. However, choosing a demultiplexing frequency is also impacted by the ambient light interference. One issue is the aliasing of harmonics of the AC power line frequency. U.S. Pat. No. 5,713,355 discusses a technique of altering the demultiplexing frequency depending upon the amount of ambient interference detected at each frequency.

U.S. Pat. No. 5,885,213 discusses subtracting a dark signal (detected ambient light) from the detected light signal. This is accomplished by leaving both the red and infrared light emitters off, in between turning them on, so that a "dark" signal supposedly composed of the ambient light present can be detected. This can then be subtracted from the desired signal. Other examples of patents dealing with the ambient light issue are U.S. Pat. Nos. 6,385,471, 5,846,190 and 4,781,195.

U.S. Pat. No. 6,449,501 discusses using a notch filter to filter out line frequency. However, the sampling rate is described as being set to twice the fundamental frequency of the power line interference, leaving higher harmonics of the power line interference as a problem, and it is unclear how the interference can be filtered without filtering the modulation frequency. Another example of a notch filter being used is set forth in U.S. Pat. No. 4,802,486, which uses a notch filter for the EKG signal.

BRIEF SUMMARY OF THE INVENTION

The present invention provides a pulse oximeter method and apparatus which provides (1) a notch filter at a distance between a demodulation frequency and a common multiple of commonly used power line frequencies (50, 60, 100, and 120) and also (2) a demodulation frequency greater than a highest pulse rate of a person and lower than any harmonic of 50, 60, 100, or 120 Hz. The invention thus allows the filtering of a significant source of ambient light interference, while choosing an optimum demodulation frequency that avoids interference from the notch filter or from harmonics of the power line interference.

In one embodiment, the common multiple is 1200, with the demodulation frequency being between 5 and 20 Hz away from 1200, preferably approximately 1211 in one embodiment.

In another aspect of the invention, dark signals, or ambient light, are measured both before and after each of the light emitter wavelengths (red and infrared in one embodiment). Instead of simply subtracting one of the dark levels, the two dark levels are averaged and then subtracted from the detected signal. This compensates for a variation in ambient light during the detected signal, reducing the effect of power line interference or any other low frequency interference.

In a another aspect of the present invention, digital filtering and decimation are done in the digital domain. When there is a change in a gain setting on the front end hardware, or in the LED power, the filters are preloaded to put values in their memory to correspond to an estimate of the settled value of the output at the new gain or power settings. This preloading speeds up when valid data will be available at the output of the filter.

DETAILED DESCRIPTION OF THE INVENTION

Overall System

Figure 1:
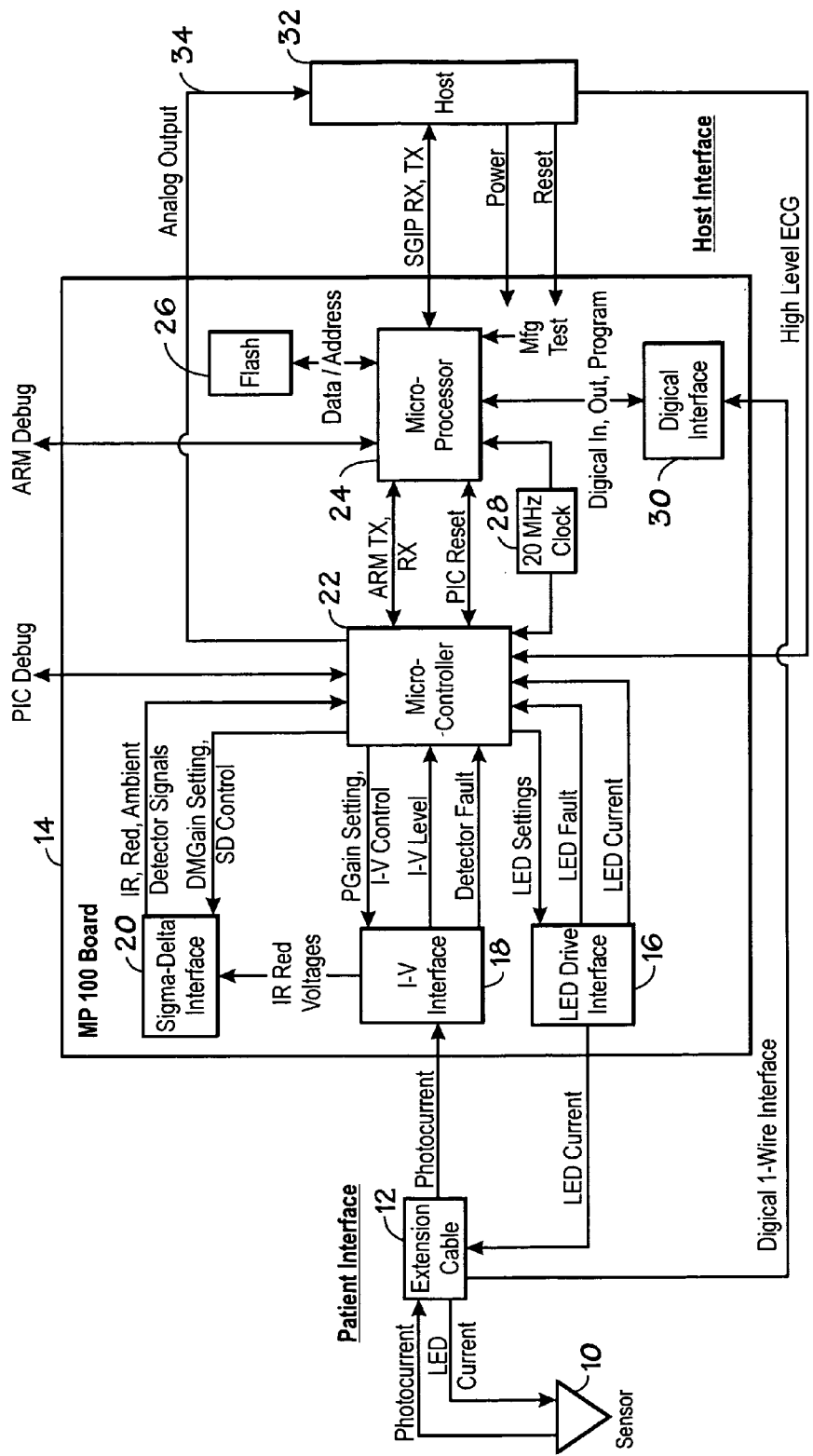
FIG. 1 is a block diagram of an oximeter incorporating the present invention.

FIG. 1 illustrates an embodiment of an oximetry system incorporating the present invention. A sensor 10 includes red and infrared LEDs and a photodetector. These are connected by a cable 12 to a board 14. LED drive current is provided by an LED drive interface 16. The received photocurrent from the sensor is provided to an I-V interface 18. The IR and red voltages are then provided to a sigma-delta interface 20 incorporating the present invention. The output of sigma-delta interface 20 is provided to a microcontroller 22. Microcontroller 22 includes flash memory for a program, and EEPROM memory for data. The oximeter also includes a microprocessor chip 24 connected to a flash memory 26. Finally, a clock 28 is used and an interface 30 to a digital calibration in the sensor 10 is provided. A separate host 32 receives the processed information, as well as receiving an analog signal on a line 34 for providing an analog display.

Notch Filter

Figure 2:
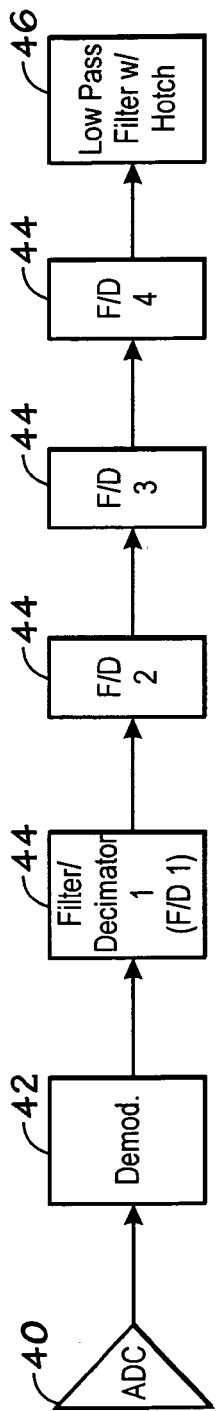
FIG. 2 is a block diagram of a portion of the digital manipulations in one embodiment of the invention, including a notch filter.

FIG. 2 shows an analog-to-digital converter 40 which provides a digital signal to be manipulated by microcontroller 22 of FIG. 1. The microprocessor would include a demodulator 42, four stages of filter/decimators 44, a low pass filter with a notch 46, as well as other blocks for digital manipulation of the signals and calculation of oxygen saturation as is well known in the art. Only the red channel is shown after the demodulation, but a similar channel is used for the IR signal.

Notch filter 46 deals with power line interference which, in the United States, comes from lights which operate on 60 Hz or 120 Hz, depending upon the power requirements. Europe and other areas use 50 Hz and 100 Hz. A common multiple of 50, 60, 100, and 120 Hz is 1200 Hz. The modulation bandwidth is chosen to be higher than the highest possible human pulse rate, preferably higher than 5 Hz. At the same time, it is chosen to be lower than any harmonic of the power line interference signals. Twenty hertz is chosen as a desirable upper limit because a second harmonic of 2450 will alias in at 2025 Hz. In one embodiment, the modulation frequency chosen is 1211.23 Hz. This is 11.23 Hz distant from 1200 Hz. (within a range of 5–20 Hz). Accordingly, in a preferred embodiment, a zero is provided in the notch filter at 11.23 Hz. The low pass filter with notch (46), in one embodiment, is an 8 pole Bessel filter with a notch at 11.25 Hz.

The present invention thus provides an effective means of eliminating interference from power line interference, such as the ripple on fluorescent lights which can alias onto the detected signal. Although anti-aliasing filters have been provided in hardware before a demodulator, it is difficult to make these effective, and thus there will be some residual line interference in the detected signal to be dealt with in the digital domain.

Averaging Ambient Dark Levels to Reduce Low Frequency Interference

Figure 3:
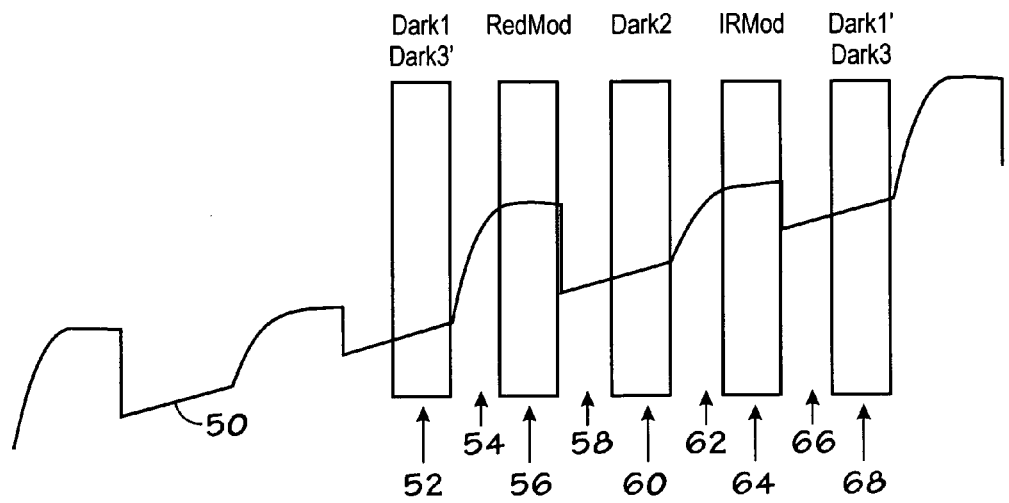
FIG. 3 is a diagram illustrating the multiple dark levels that are averaged in an embodiment of the invention.

FIG. 3 illustrates another aspect of the present invention, reducing ambient interference by averaging the ambient dark levels before and after a sampling period to account for low frequency interference from power lines or other sources. FIG. 3 shows a signal at a sampling rate of 2400. The upward sloping line in FIG. 3 is due to 60 Hz power line interference. It is desirable to eliminate the effect of this upward slope (which will be downward on other parts of the 60 Hz (or 50 Hz, etc.) signal.

FIG. 3 shows a detected signal during different periods of modulation. The detected signal level is illustrated by a line 50. During a first dark period 52, neither the red nor IR LED are on, allowing a sampling of the dark, or ambient, light. After this sampling, during a time period 54, the red LED is turned on, with signal 50 rising during this period as the red LED comes on to its full intensity. During the time period 56, the detected signal corresponds to the red LED being on. After the red LED is turned off and the signal decays during a period 58, a second dark period 60 is sampled.

Subsequently, the IR LED is turned on during a period 62, and sampled during a period 64. It is turned off and the signal decays during a period 66, with a third dark sample being taken during a period 68. The third dark sample also corresponds to the first dark period 52, as the process repeats itself.

As can be seen from FIG. 3, if only one of the dark levels is used, an inaccurate ambient level may be measured if the ambient level is varying, such as due to a low frequency interference. By averaging the dark periods before and after the sampling period for a particular wavelength, a more accurate measurement of the ambient dark level signal is obtained. For example, the ambient interference during the red modulation period 56 is determined by measuring the dark 1 signal during period 52 and the dark 2 signal during period 60 and averaging these signals. Similarly, for the infrared modulation period 64, the dark 2 signal during period 60 and the dark 3 signal during period 68 are averaged and subtracted from the detected IR signal to eliminate the ambient interference. All of these calculations are done in the digital domain by microcontroller 22 of FIG. 1.

Preloading Decimation and Bessel Filters

Figure 4:
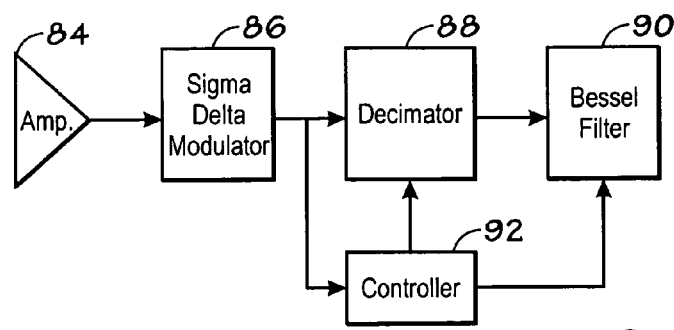
FIG. 4 is a diagram illustrating the preloading of the digital filter and decimator according to an embodiment of the present invention.

FIG. 4 illustrates another aspect of the present invention where filters and software are preloaded. Before the analog input signal is processed through the sigma-delta modulator and the multi-bit analog-to-digital converter, it is typically amplified in a hardware amplifier 84. After processing by the sigma-delta modulator 86 and conversion into digital domain, it is decimated to reduce the sample rate by a decimator 88 and filtered by a Bessel filter 90. A controller 92 pre-loads the memories of the Bessel filter and decimator with an estimate of what the settled value of the output would be. This will significantly reduce the settling time of the filter after a step change in its input. Such a step change in the input can occur from a change in the gain settings of the amplifier 84. Alternately, a step change can be the result of a change in the particular LED being activated, the power of the LED, or other gain settings of the front end hardware. Since the controller 92 would be activating such changes, it will have the knowledge of when to pre-load the filter and decimator with the appropriate values. Although these are shown as blocks in FIG. 4, it is understood that in the preferred embodiment this is done by a software program which functions as controller 92, filter 90 and decimator 88. This preloading of the filter and decimator provides that valid data is available sooner by shortening the settling time.

As will be understood by those skilled in the art, the present invention may be embodied in other specific forms without departing from the essential characteristics thereof. For example, more than two different wavelengths of light could be used. Alternately, a different demodulation frequency could be chosen. In addition, the notch filtering can be done either before or after other digital processing of the detected signal. Accordingly, the foregoing description is intended to be illustrative, but not limiting, of the scope of the invention which is set forth in the following claims.

What is claimed is:

1. A method for operating a pulse oximeter, comprising:
   alternately generating light at two wavelengths using a modulation frequency that is a predetermined distance from a common multiple of 50, 60, 100, and 120, where the predetermined distance is greater than a highest pulse rate of a person and lower than a distance of any harmonic of 50, 60, 100, or 120;
   directing the light at a tissue site;

detecting a received light signal from the tissue site;
processing the received light signal to generate a processed signal;
notch filtering the processed signal at a frequency equivalent to the predetermined distance to produce a filtered signal; and
calculating at least one patient characteristic based on the filtered signal.

2. The method of claim 1 wherein processing the received light signal comprises digitizing the processed signal.

3. The method of claim 1 wherein the common multiple comprises 1200.

4. The method of claim 1 wherein the predetermined distance is between 5 and 20 hertz.

5. The method of claim 1 wherein the predetermined distance is approximately 11 hertz.

6. The method of claim 1 wherein the notch filtering is performed by providing a zero in a digital filter at the predetermined distance.

7. The method of claim 1 wherein calculating at least one patient characteristic comprises calculating a blood flow characteristic.

8. A method for measuring a detected light signal in a pulse oximeter comprising:
alternately generating light using a modulation frequency to alternate between a first period of time when a first wavelength is being generated, a dark period of time when no light is being generated, and a second period of time when a second wavelength is being generated;
directing the light at a tissue site;
detecting a received light signal from the tissue site;
estimating a first level of ambient light in the received light signal during the first period of time by averaging detected light received during the dark periods before and after the first period;
estimating a second level of ambient light in the received light signal during the second period of time by averaging detected light received during the dark periods before and after the second period;
calculating a total light signal by subtracting the first level of ambient light from the received light signal generated during the first period of time and subtracting the second level of ambient light from the received light signal generated during the second period of time; and
calculating at least one patient characteristic based on the total light signal.

9. The method of claim 8 wherein calculating at least one patient characteristic comprises calculating a blood flow characteristic.

10. A pulse oximeter comprising:
a control circuit configured to supply a control signal;
at least one light emitter configured to receive the control signal and, based on the control signal, to alternately generate light at two wavelengths using a modulation frequency that is a predetermined distance from a common multiple of 50, 60, 100, and 120 where
the predetermined distance is greater than a highest pulse rate of a person and lower than a distance of any harmonic of 50, 60, 100, or 120;
a detector configured to detect a received light signal from a tissue site;
a processing circuit configured to process the light signal to generate a processed signal; and
a notch filter configured to filter the processed signal at a frequency equivalent to the predetermined distance.

11. The pulse oximeter of claim 10 comprising:
an analog-to-digital converter configured to digitized the process signal.

12. The pulse oximeter of claim 10 wherein the common multiple comprises 1200.

13. The pulse oximeter of claim 10 wherein the predetermined distance is between 5 and 20 hertz.

14. The pulse oximeter of claim 10 wherein the predetermined distance is approximately 11 hertz.

15. The pulse oximeter of claim 10 wherein the notch filter provides a zero in a digital filter at the predetermined distance.

16. A pulse oximeter comprising:
a control circuit configured to supply a control signal;
at least one light emitter configured to receive a control signal and, based on the control signal, to alternately generate light at two wavelengths using a modulation frequency to alternate between a first period of time when a first wavelength is being generated, a dark period of time when no light is being generated, and a second period of time when a second wavelength is being generated;
a detector configured to detect a received light signal from a tissue site;
a processing circuit configured to estimate a first level of ambient light in the received light signal during the first period of time by averaging detected light signal received during the dark periods before and after the first period, and to estimate a second level of ambient light in the received light signal during the second period of time by averaging detected light dark periods before and after the second period;
the processing circuit further configured to calculate a total light signal by subtracting the first level of ambient light from the received light signal generated during the first period of time and subtracting the second level of ambient light from the received light signal generated during the second period of time and configured to calculate at least one patient characteristic based on the total light signal.

17. The pulse oximeter of claim 16 wherein the at least one patient characteristic is a blood flow characteristic.

18. A pulse oximeter comprising:
a processing circuit configured to;
supply a control signal capable of controlling a light emitter to alternately generate light at two wavelengths using a modulation frequency that is a predetermined distance from a common multiple of 50, 60, 100 and 120, where the predetermined distance is greater than a highest pulse rate of a person and lower than a distance of any harmonic of 50, 60, 100 or 120;
process detected light signals to generate a processed signal; and
notch filter the processed signal at a frequency equivalent to the predetermined distance.

19. The pulse oximeter of claim 18 wherein the processing circuit is configured to calculate at least one patient characteristic based on the filtered process signal.

20. The pulse oximeter of claim 19 wherein the at least one patient characteristic is a blood flow characteristic.

21. The pulse oximeter of claim 18 wherein the common multiple comprises 1200.

22. The pulse oximeter of claim 18 wherein the predetermined distance is between 5 and 20 hertz.

23. The pulse oximeter of claim 18 wherein the processing circuit comprises a notch filter that provides a zero in a digital filter at the predetermined distance.

24. A pulse oximeter comprising:

a processor circuit configured to:

supply a control signal capable of controlling a light emitter to alternately generate light at two wavelengths using a modulation frequency to alternate between a first period of time when a first wavelength is being generated, a dark period of time when no light is being generated, and a second period of time when a second wavelength is being generated;

estimate a first level of ambient light in received light signals during the first period of time by averaging detected light received during the dark periods before and after the first period, and to estimate a second level of ambient light in received light signals during the second period of time by averaging detected light dark periods before and after the second period;

calculate a total light signal by subtracting the first level of ambient light from received light signals generated during the first period of time and subtracting the second level of ambient light from received light signals generated during the second period of time; and calculate at least one patient characteristic based on the total light signal.

25. The pulse oximeter of claim 24 wherein the at least one patient characteristic is a blood flow characteristic.

\* \* \* \* \*